United States Patent
Lackey

(10) Patent No.: US 6,770,598 B1
(45) Date of Patent: Aug. 3, 2004

(54) PROTEIN TRANSPORT ENHANCER FOR TRANSGENIC PLANTS

(75) Inventor: James Lackey, Portland, TX (US)

(73) Assignee: LTA Resources Management, Taft, TX (US)

( * ) Notice: Subject to any disclaimer, the term of this patent is extended or adjusted under 35 U.S.C. 154(b) by 0 days.

(21) Appl. No.: 10/429,974

(22) Filed: May 6, 2003

(51) Int. Cl.$^7$ .......................... A01N 43/40; A01N 31/00
(52) U.S. Cl. ........................................ 504/254; 504/354
(58) Field of Search ................................. 504/254, 354

(56) References Cited

U.S. PATENT DOCUMENTS

| | | |
|---|---|---|
| 5,578,702 A | 11/1996 | Adang |
| 6,020,288 A | 2/2000 | Nonomura et al. |
| 6,291,156 B1 | 9/2001 | Estruch et al. |
| 6,294,711 B1 | 9/2001 | Meulewaeter et al. |
| 6,331,531 B1 | 12/2001 | Kern |
| 6,331,665 B1 | 12/2001 | Lundquist et al. |
| 2002/0038005 A1 | 3/2002 | Wojciechowska et al. |

OTHER PUBLICATIONS

"An Australian approach to IPM in cotton: integrating new technologies to minimise insecticide dependence"; Gary P. Fitt; 2000; pp. 793–800.
"Atonik: A Plant Growth Enhancer to Increase Yield in Cotton"; C. Guo et al.; 1995; pp. 1–7.
"Emerging Technologies for Integrated Pest Management Concepts, Research, and Implementation"; George G. Kennedy and Turner B. Sutton; 1999.

*Primary Examiner*—S. Mark Clardy
(74) *Attorney, Agent, or Firm*—Roylance, Abrams, Berdo & Goodman, LLP

(57) ABSTRACT

Expression and stability of desirable proteins in transgenic plants are promoted and maintained by treatment with a protein transport enhancer. Preferably, the transgenic plant is a commodity crop that has been modified to express pesticidally effective protein proteins.

8 Claims, No Drawings

PROTEIN TRANSPORT ENHANCER FOR TRANSGENIC PLANTS

FIELD OF INVENTION

The invention relates to a method for the treatment of transgenic plants, especially crop plants that are designed to express pesticidally effective proteins.

BACKGROUND OF THE INVENTION

Transgenic plants have had a significant impact on commercial agriculture, with promising benefits but raising new pest management issues. Notably, agricultural crops based on plants that have been modified with pesticidally effective crystal protein genes to express pesticidally effective proteins hold the promise of selectively targeting pests by making their food source (the plant tissues) toxic thereby reducing or eliminating the amount of chemical insecticides that are used to control pest populations.

Certain members of the gram positive bacteria belonging to the genus Bacillus produce proteins that are insecticidal. The most well characterized are those of *Bacillus thuringiensis* (*BT*), where the insecticidal proteins are found as crystalline bodies with sporulating bacteria. The insecticidal crystal proteins are characterised by their potency and specificity towards specific insect pests, many of which are agronomically important, and their relative safety to non-target insect species and vertebrates, particularly humans. They have enjoyed a long history of use in horticultural industries where the mixture of crystals and spores are sprayed just like a chemical pesticide, but they have not been used with much success on broad-acre field crops.

The insecticidal crystals are composed of a large protein that is essentially inactive. When a caterpillar ingests some of the insecticidal crystals, the alkaline reducing conditions of the insects midgut cause the crystals to dissociate and release the crystal protein. At this stage the protein toxin is inactive, but specific proteases within the gastric juices of the insect chop the protein down to its protease resistant core that is now fully active. This activated insecticidal protein then binds to a specific receptor on the brush border membranes of the cells lining the midgut and inserts itself into the cells membrane. When about eight of these aggregate together, they form a pore or channel through the membrane, and allow the cell contents to leak out causing the death of the cells essential for nutrient absorption. The insects rapidly stop feeding and eventually starve to death or die from secondary bacterial infections within about 24 hours. The processes of crystal solublization, proteolytic processing to an active insecticidal protein and the binding to a specific receptor, all make the *BT* proteins highly specific and very desirable from an environmental perspective.

Many thousands of different isolates of *B. thuringiensis* have been collected and their insecticidal protein content and activity spectrums determined. A large number of *BT*-insecticidal protein genes have also now been cloned and sequenced. To avoid any confusion researchers have proposed a uniform naming system for the crystal protein genes (Cry genes) based on their protein sequence and the types of insects for which they were toxic.

TABLE 1

| Gene Type | Insect Host | Size (kD) |
|---|---|---|
| Cry IA | Caterpillars | 133.2 |
| Cry IB | Caterpillars | 138.0 |
| Cry IC | Caterpillars | 134.8 |
| Cry IIA | Caterpillars/ | 70.9 |
| Cry IIB | Fly larvae | 70.8 |
| Cry IIIA | Beetle larvae | 73.1 |
| Cry IVA | Fly larvae | 134.4 |
| Cry IVB | Fly larvae | 127.8 |
| Cry IVC | Fly larvae | 77.8 |
| Cry IVD | Fly larvae | 72.4 |

The proteins encoded by the Cry I genes are all similar in protein sequence and are toxic only to caterpillars, ie. the larvae of moths and butterflies (Lepidoptera); the Cry II genes encode proteins toxic to Lepidoptera and/or Diptera (flies and mosquitoes) while the Cry IV proteins are only active against Diptera. Cry III genes produce proteins active against beetle (Coleoptera) larvae. Within these major groupings smaller divisions have been made by considering the similarities or differences between the different protein sequences. The Cry I group, for example was originally divided into Cry IA, IB and IC (although it is now up to Cry IG) where the different sub-groups may only be 50% identical at the protein sequence level. Finer sub-divisions have also been made and Cry IA now consists of Cry IA(a), IA(b) and IA(c).

A number of methods have been developed for introducing desired genes into crop plant cells and growing fertile plants therefrom. See, U.S. Pat. No. 6,329,574 and http://www.cotton.pi.csiro.au/publicat/pest/transgen.htm, the contents of which are herein incorporated by reference. The method of choice depends in part upon the target species, but cotton modification often rely on a natural gene transfer agent that has evolved its own method of plant genetic engineering. The disease called Crown Gall is a plant tumor disease caused by the soil-borne bacterial pathogen, Agrobacterium tumefaciens. In the early 70's it was recognized that the bacterium caused the disease by transferring some of its own genetic material into the DNA of the plant cells that it infected. These parasitic genes subverted the normal biochemical machinery of the infected cells and caused them to make novel compounds that only the bacterium could utilize. This process of genetic colonization by the bacterium was just what genetic engineers were looking for, provided that they could stop the bacterium causing the disease symptoms. After further study scientists were able to identify which genes caused the disease and because bacteria are much simpler organisms to genetically manipulate, they were able to replace the disease-causing genes with the novel genes they were constructing from parts of potentially useful genes. The bacterium could then be used to piggy-back genes from the test-tube into plant cells. However not all plant cells exposed to the bacterium eventually receive the novel genes. Removal of unmodified plant cells from modified cells uses antibiotic purification.

Plant cells are sensitive to many of the antibiotics that are used to control bacterial infections in animals and humans. If a gene could be isolated that gave the plant cells tolerance to one of these toxic antibiotics then if physically linked to some desirable gene and inserted into the Agrobacterium, it would provide a useful selection system to kill off those cells that don't receive the genes during the "infection" process. Genes have been known in bacteria for many years that give the bacteria resistance to antibiotics by producing enzymes that breakdown or chemically modify the antibiotic so that it is no longer toxic. Using the techniques of gene splicing described above researchers have been able to modify a bacterial gene that encodes an enzyme that detoxifies the antibiotic kanamycin and have produced a new hybrid gene that causes the production of this enzyme in plant cells and prevents their death in the presence of potentially lethal doses of kanamycin. Combining this antibiotic selection system with plant tissue culture procedures it has been possible to use Agrobacterium to deliver genes into a wide variety of plants from petunias to cottons.

Cotton is a crop of particular interest. Commercially available forms of transgenic cotton use the CryIAc (BOLLGARD™ by Monsanto) or a combination of CryIAc with Cry2Ab (BOLLGARD™ II by Monsanto) genes to express the endotoxin protein of *B. thuringiensis*. Field efficacy reports indicate a 50–70% reduction in the amount of applied pesticide needed to control the pests *Helicoverpa armigera* and *H. punctigera*. Also of interest are crop plants modofied with the *B. thuringiensis* crystal toxin genes designated cryET33 and cryET34 which encode the colepteran-toxic crystal proteins, CryET33 (29-kDa) crystal protein, and the cryET34 gene encodes the 14-kDa CryET34 crystal protein. The CryET33 and CryET34 crystal proteins are toxic to red flour beetle larvae and Japanese beetle larvae. (See, U.S. Pat. No. 6,399,330.)

The use of transgenic crop plants raises new issues in the ongoing struggle towards integrated pest management. Some of these issues concern a reduction in the amount of expressed endotoxin as the plants mature which leads to a loss of efficacy in the latter stages of the growing season (the last ⅓ of the cotton growing season) and the increased probability of surviving pests that can develop immunity to the endotoxin. Such drawbacks have lead to the development of pest control strategies that dictate a planting "window" relative to the development cycle of local pests and designated pest population minimum threshold values for pesticide application.

Physiological stress and physical damage to the transgenic plants can also result in a reduction of expressed endotoxin protein with a corresponding drop in pest control efficacy. Thus, an extended drought and/or high temperatures can reduce the endotoxin expression rate in the transgenic crop and provide a significant drop in pest protection that can dictate the need for pesticide spraying.

The specific reasons for the drop in endotoxin protein expression are not well understood. In *BT* cotton, it is theorized that expression of the CryIAc gene drops because the CMV35S promoter concentration declines, the gene is "silenced, or other post-transcription events. It is also thought that the CryIAc protein is reduced due to increased turnover, sequestration within the plant, or dilution due to growth and aging. It is understood that CryIAc transription levels are unstable in both immature and mature *BT* cotton plants.

It would be desirable to have a system for treating transgenic plants designed to express pesticidally effective proteins that would promote the expression of these proteins despite increasing plant maturity, physiological stress, and physical damage.

SUMMARY OF THE INVENTION

It is an objective of the invention to provide a method for treating transgenic plants, preferably transgenic crops that express pesticidal proteins, and especially for transgenic crops that express insecticidal proteins.

It is another objective of the invention to provide a method for extending the period over which expressed proteins are present in sufficient quantity to control pest insect populations feeding on the treated plants.

In accordance with these and other objectives that will become apparent from the description herein, a method for treating transgenic crop plants according to the invention comprises applying to foliage of transgenic plants that are designed to express pesticidally effective proteins a protein transport enhancer that promotes the expression and/or stability of pesticidally effective proteins within the treated plants.

Although not wishing to be bound by any particular theory of operation, it is thought that the protein transport enhancer acts in one or more of several ways: (a) as a form of protective water substitute for cellular membranes during times of water deprivation stress, (b) as a protein stabilizer for the desired pesticidal protein, and/or (c) as a binder for proteins that facilitates movement via intraplant transport mechanisms. The result is that transgenic crop plants treated according to the invention express and move pesticidally effective proteins into fruit tissues despite physiological stress from water shortage and plant damage. It is thought that the treatment according to the invention will also continue to express effective levels of pesticidal protein through plant growth and maturity.

DETAILED DESCRIPTION OF THE INVENTION

Transgenic plants are treated, according to the invention, with a protein transport enhancer that stimulates and/or protects cellular expression and intraplant transport mechanisms sufficiently that desired levels of pesticidal protein proteins are maintained in plant tissues, fruits, and seeds despite water deprivation, physical damage to plant tissues, growth, and plant maturity. Maintenance of desired protein expression levels and concentrations of protein proteins within transgenic plant tissues help to maintain efficacy levels for better pest control, further reductions in amounts of applied pesticides now required to counteract reductions in efficacy, and should help to prevent survival of exposed pests and the development of resistant pest populations.

It will be understood that all percentages identified herein are by weight with respect to the total weight of product, unless otherwise noted.

Suitable protein transport enhancers for use in the present invention include one or more compounds and agrichemically acceptable salts of compounds according to the structure in Formula 1:

Formula 1

$$\underset{Z}{\underset{\|}{X}} \underset{\|}{\bigcirc} \underset{}{Y}$$

wherein:
X is $NO_2$,
Y is H, $C_1$–$C_6$ alkyl, $C_1$–$C_6$ alkyloxy, $C_2$–$C_6$ alkenyl, and
Z is C or N.

In particular, moiety Y can be methyl, ethyl, propyl, butyl, iso-butyl, pentyl, hexyl, methoxy, ethoxy, propoxy, butoxy, iso-butoxy, pentoxy, and hexoxy.

Preferably protein transport enhancers used in the present invention include one or more compounds and salts of compounds according to the above structure in which X is a nitro group at the ortho or para positions relative to the hydroxy group, Y is hydrogen or a $C_1$–$C_3$ alkyloxy, and Z is a carbon atom. Suitable salts include water soluble alkali metal salts (especially sodium and potassium salts), ammonium salts, and other water soluble salts that are not phytotoxic or of environmental concern.

The most preferred protein transport enhancer includes a combination of the sodium salts of p-nitrophenolate (A), o-nitrophenolate (B), and 2-methoxy-5-nitrophenolate (C). It is particularly preferred that the protein transport enhancer contain a mixture of these salts in a range of ratios within the range of A:B:C of (0.1–10):(0.1–10):1. A commercial source of these salts is available under the name ATONIK® Asahi Chemical Mfg. Co., Ltd. at a ratio of A:B:C of 2:3:1.

Protein transport enhancers according to the invention are applied at a rate generally less than 20 grams of each active ingredient per acre of treated field (gAI/ac). Preferably, these enhancers are applied at a rate within the range of 1–20 gAI/ac and most preferably at a rate within the range of 3–18 gAI/ac. It is especially preferred when salts of the protein transport enhancers are used within the range of 0.01–5 wt % based on total weight and applied at a rate (combined) within the range of 0.5–20 fluid ounces per acre (oz/ac).

Protein transport enhancers according to the invention can be applied in combination with one or more active ingredients, spray aids, spreading agents, or additional agents suitable for agricultural use on the target plant. Exemplary active ingredients that can be applied with the protein transport enhancer of the invention include herbicides, plant growth enhancing agents, plant growth stunting agents, foliar fertilizers, fungicides (external and systemic), and insecticides (external and systemic).

Herbicides that can be used include the triazines (e.g., atrazine), the ureas, glyphosate, sulfosate, glyfosinate, and sethoxydim.

Suitable plant growth enhancing agents for the present invention include plant growth hormones such as at least one of the 84 identified gibberillins with $GA_3$, $GA_4$, $GA_5$, $GA_7$ and $GA_9$ being preferred; cytokinins (e.g., zeatin, kinetin, benzyladenine, dihydrozeatin, and isopentenyl adenine); auxins (e.g., indolacetic acid (IAA), indolebutyric acid (IBA), and naphthalenacetic acid (NAA)); and polyhydroxycarboxylic acids of 2, 4, 5, and 6 carbon structures; ethephon; and fertilizers.

Suitable plant growth stunting agents useful in the invention include chlornequat chloride, mepiquat chloride, as well as maleic hydrazide and its esters. Such plant growth regulators affect and alter plant metabolic processes to enhance or retard plant growth. All such agents can be used according to the application rates and timing specified by the manufacturer on the product label.

Systemic fungicides that will benefit from the invention include tridemorph, metalaxyl, iprodione, fosetyl-aluminum, thiophanate, benomyl, triadimefon, carboxin, oxycarboxin, carbendazim, thiabendazole, thiophanate, ethirimol, bupirimate, and dimethirimol.

Suitable systemic insecticides include aldicarb, acephate, carbofuran, dimethoate, phorate, and terbufos.

The specific mechanisms by which the expression and transport mechanisms are effected are not well known. For example, tests on unmodified wheat with radiolabeled nitrophenolate salts have tracked the treatment agent to proteins transported to the seed kernel in wheat plants. Another study suggests that phenolic agents act as hydration agents for cellular membranes.

In cotton, it is recognized that cotton seed requires high amounts of protein, and seeds produce lint from carbohydrates within the plant system. Tests with ATONIK® on normal (i.e., not genetically modified or otherwise altered to express pesticidal proteins as a normal part of plant metabolism function) show an increased yield of seed and lint. Such an effect is consistent with action as a plant growth regulator, but does not necessarily suggest anything regarding the effect of treating plants that have been genetically modified to produce a designated protein as part of the normal plant function.

Transgenic plants that can be treated according to the invention are generally those that have been modified from wild type to contain a gene that expresses a desired pesticidally effective protein sequence. Preferably, the transgenic plant includes genes that express pesticidally effective proteins that are effective to provide resistance against attacks or infections by insects, bacteria, fungus, mildew, mold, mites, and the like.

Two genes of particular effectiveness are the CryIAc gene (driven by the CMV35S promoter) and the Cry2Ab gene. These genes can be inserted individually or in combination into cotton, corn, wheat, sorghum, soybeans, and similar agricultural commodity crops to provide pesticidally effective protection against a variety of pest insects. Of special interest is cotton stock that has been modified to express pesticidally effective protein proteins (e.g., *BT* cotton). Seed stock for *BT* cotton that can be treated according to the invention is commercially available from several sources under the tradename BOLLGARD™ or BOLLGARD™ II (Monsanto Co.).

Protein transport enhancers according to the invention are applied to transgenic plants at rates and times in the plant's growing cycle or season so as to maintain pesticide protein expression and stabilization within plant tissues. The table below identifies preferred transgenic plants to be treated and the amount of protein transport enhancer to be applied within generally useful, preferred, and more preferred application rates.

TABLE 1

| TRANSGENIC PLANT | APPLICATION RATE (OZ/AC) | PREFERRED APPLICATION RATE (OZ/AC) | MORE PREFERRED APPLICATION RATE (OZ/AC) |
|---|---|---|---|
| Bt cotton | 1–100 | 1–50 | 5–30 |
| Bt corn | 1–100 | 1–50 | 5–30 |

EXAMPLES

Transgenic *Bt* cotton (Deltapine Nucotn B) and unmodified cotton plants in two liter pots in a controlled environment were sprayed with ATONIK®, a commercially available product containing a mixture of agents thought to be general growth regulating agents but which appears to act well as protein transport enhancers for genetically modified commodity crop plants. ATONIK® contains the sodium salts of p-nitrophenolate (0.3%), o-nitrophenolate (0.2%), and 5-nitroguaiacolate (0.1%). Cotton plants were treated at at $7^{th}$ true leaf (TL) and sampled 10 days later for the upper expanded main stem leaf. The temperature was maintained within the range of 76–86° F. with adequate watering. After sampling ($7^{th}$ TL+10 days), the plants were again sprayed with ATONIK® and subjected to stress from an elevated temperature (86–102° F.) and inadequate water supply (drought conditions) until they were sampled 5 days later ($7^{th}$ TL+15 days) for expanded upper main stem leaf. Five days thereafter ($7^{th}$ TL+20 days) under the same conditions, the plants were sampled for leaf and squares.

After each sampling, tissue samples were placed in sealed bag and immediately taken to a facility for bollworm feeding tests. Bollworm mortality was measured at 24, 48, 72 and 96 hrs from initiation of feeding for the first spray application samples and at 72 and 96 hrs for the 2$^{nd}$ spray application samples.

Once the mortality study was completed, a leaf profile from representative cotton plants was taken for protein analysis. Leaves were collected at nodes 2, 6, 8, and 10 (counting from the top) and stored at −80° F.

The bollworm mortality for collected leaves in the first collected sample (7$^{th}$ TL +10 days) are shown in Table 2.

TABLE 2

| 1$^{st}$ Treatment | Bollworm Mortality (% dead at 7$^{th}$ TL + 10 days) | | | |
|---|---|---|---|---|
| | 24 hrs | 48 hrs | 72 hrs | 96 hrs |
| Control (Bt cotton) | 0 | 28.3 | 56.7 | 58.3 |
| ATONIK 5 oz/ac | 0 | 35.0 | 60.0 | 68.3 |
| ATONIK 10 oz/ac | 1.7 | 43.3 | 61.7 | 71.7 |
| ATONIK 20 oz/ac | 3.3 | 60.0 | 78.3 | 81.7 |
| Control (non-Bt cotton) | 0 | 1.7 | 1.7 | 3.3 |

The bollworm mortality from leaves collected at five and 10 days after the second spraying are reported in Table 3.

TABLE 3

| 2$^{nd}$ Treatment | Bollworm Mortality (% dead at 7$^{th}$ TL + X days) | | | |
|---|---|---|---|---|
| | 15 Days | | 20 Days | |
| | 72 hrs | 96 hrs | 72 hrs | 96 hrs |
| Control (Bt cotton) | 68.3 | 71.1 | 90.0 | 95.0 |
| ATONIK 5 oz/ac | 63.3 | 71.1 | 81.7 | 91.7 |
| ATONIK 10 oz/ac | 85.0 | 90.0 | 85.0 | 96.7 |
| ATONIK 20 oz/ac | 83.3 | 90.0 | 90.0 | 98.3 |
| Control (non-Bt cotton) | 0 | 0 | 5.0 | 6.7 |

The bollworm mortality from squares collected at 7$^{th}$ TL+20 days (2$^{nd}$ treatment) spraying are reported in Table 4.

TABLE 4

| 2$^{nd}$ Treatment | Bollworm Mortality (% dead at 7$^{th}$ TL + 20 days) | |
|---|---|---|
| | 72 hrs | 96 hrs |
| Control (Bt cotton) | 75.0 | 81.7 |
| ATONIK 5 oz/ac | 95.0 | 98.3 |
| ATONIK 10 oz/ac | 88.3 | 93.3 |
| ATONIK 20 oz/ac | 86.7 | 95.0 |
| Control (non-Bt cotton) | 0 | 3.3 |

Table 5 shows the effect of treatments with ATONIK on the height and number of nodes in *Bt* cotton.

TABLE 5

| Treatment | Plant Height (cm) | No. of Nodes (avg) |
|---|---|---|
| Control (Bt cotton) | 63.5 | 16.7 |
| ATONIK 5 oz/ac | 61.7 | 15.8 |
| ATONIK 10 oz/ac | 62.0 | 16.0 |
| ATONIK 20 oz/ac | 62.2 | 17.0 |
| Control (non-Bt cotton) | 61.0 | 13.8 |

The results show that treatment with the protein transport enhancer according to the invention resulted in higher bollworm mortality under both optimum growth conditions (Table 2) and under stress conditions from both temperature and lack of water (Tables 3 and 4). Treatment with ATONIK did not, however, result in increased vegetative growth (Table 5).

What is claimed is:

1. A method for maintaining the pesticidal efficacy of transgenic plants that include a gene which expresses a pesticidally effective protein, said method comprising:

treating said transgenic plants with a protein transport enhancer that stabilizes transport of pesticidally effective proteins within said plant.

2. A method according to claim 1 wherein said transgenic plant is cotton or corn.

3. A method according to claim 1 wherein said transgenic plant is cotton that has been modified to express *B. thuringiensis* protein.

4. A method according to claim 1 wherein said protein transport enhancer comprises a mixture of phenolate and nitroguaiacolate salts.

5. A method according to claim 4 wherein said protein transport enhancer is applied to said plants at a rate within the range of 1–100 oz/acre.

6. A method according to claim 5 wherein said protein transport enhancer is applied to said plants at a rate within the range of 1–50 oz/acre.

7. A method according to claim 6 wherein said protein transport enhancer is applied to said plants at a rate within the range of 5–30 oz/acre.

8. A method according to claim 1 wherein said protein transport enhancer comprises polyols obtained from reduction of aldo- and keto- groups in a carbohydrate.

* * * * *